United States Patent [19]

Mitchell et al.

[11] Patent Number: 5,141,842
[45] Date of Patent: Aug. 25, 1992

[54] RADIATION-SENSITIVE COMPOSITIONS COMPRISING A PHOTOCROSSLINKABLE POLYMER, A LEUCO DYE, A PHOTOOXIDANT AND A HETEROAROMATIC AMINE N-OXIDE

[75] Inventors: James E. Mitchell, Windsor; Paul R. West; Paul R. Josephson, Jr., both of Fort Collins, all of Colo.

[73] Assignee: Eastman Kodak Company, Rochester, N.Y.

[21] Appl. No.: 676,131

[22] Filed: Mar. 27, 1991

[51] Int. Cl.⁵ .............................. G03F 7/038
[52] U.S. Cl. ........................ 430/285; 430/286; 430/292
[58] Field of Search ............ 430/285, 286, 342, 340, 430/338, 292; 522/108, 104

[56] References Cited

U.S. PATENT DOCUMENTS

| | | | |
|---|---|---|---|
| 3,359,109 | 12/1967 | Harder et al. | 96/90 |
| 3,481,739 | 12/1969 | Wainer et al. | 96/90 |
| 3,582,342 | 6/1971 | Itano et al. | 96/90 |
| 3,615,454 | 10/1971 | Cescon et al. | 430/292 |
| 3,827,887 | 8/1974 | Hazy et al. | 96/480 |
| 4,251,619 | 2/1981 | Kurita | 430/292 |
| 4,425,424 | 1/1984 | Altland et al. | 430/270 |

Primary Examiner—Cynthia Hamilton
Attorney, Agent, or Firm—Alfred P. Lorenzo

[57] ABSTRACT

Radiation-sensitive compositions which are especially useful in the production of negative-working lithographic printing plates comprise a photocrosslinkable polymer, containing the photosensitive group

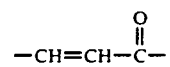

as an integral part of the polymer backbone, and a print-out composition which produces an optical density difference upon exposure to activating radiation and thereby enables the exposed image on the printing plate to be seen before the plate is processed. The print-out composition comprises a leuco form of a dye having one or more removable hydrogen atoms, the removal of which forms a compound colored differently from the leuco form; a photooxidant which has a photoscissionable nitrogen-oxygen bond, the photooxidant serving to convert the leuco dye to the differently colored form when the composition is exposed to activating radiation; and a heteroaromatic amine N-oxide which functions to improve the photo-efficiency of the print-out composition and thereby increase the print-out density.

26 Claims, No Drawings

RADIATION-SENSITIVE COMPOSITIONS COMPRISING A PHOTOCROSSLINKABLE POLYMER, A LEUCO DYE, A PHOTOOXIDANT AND A HETEROAROMATIC AMINE N-OXIDE

FIELD OF THE INVENTION

This invention relates in general to radiation-sensitive compositions and in particular to radiation-sensitive compositions which contain a photocrosslinkable polymer. More specifically, this invention relates to improved radiation-sensitive compositions containing both a photocrosslinkable polymer and a print-out composition which provides a visual print-out of exposure to activating radiation. Such compositions are especially useful in the production of lithographic printing plates.

BACKGROUND OF THE INVENTION

The art of lithographic printing is based upon the immiscibility of oil and water, wherein the oily material or ink is preferentially retained by the image area and the water or fountain solution is preferentially retained by the non-image area. When a suitably prepared surface is moistened with water and an ink is then applied, the background or non-image area retains the water and repels the ink while the image area accepts the ink and repels the water. The ink on the image area is then transferred to the surface of a material upon which the image is to be reproduced, such as paper, cloth and the like. Commonly the ink is transferred to an intermediate material called the blanket, which in turn transfers the ink to the surface of the material upon which the image is to be reproduced.

Negative-working lithographic printing plates are prepared from negative-working radiation-sensitive compositions that are formed from polymers which crosslink in radiation-exposed areas. A developing solution is used to remove the unexposed portions of the coating to thereby form a negative image.

The most widely used type of negative-working lithographic printing plate comprises a layer of a radiation-sensitive composition applied to an aluminum substrate and commonly includes a subbing layer or interlayer to control the bonding of the radiation-sensitive layer to the substrate. The aluminum substrate is typically provided with an anodized coating formed by anodically oxidizing the aluminum in an aqueous electrolyte solution.

It is well known to prepare negative-working lithographic printing plates utilizing a radiation-sensitive composition which includes a photocrosslinkable polymer containing the photosensitive group:

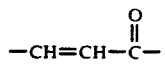

as an integral part of the polymer backbone. (See, for example, U.S. Pat. Nos. 3,030,208, 3,622,320, 3,702,765 and 3,929,489). A typical example of such a photocrosslinkable polymer is the polyester prepared from diethyl p-phenylenediacrylate and 1,4-bis(β-hydroxyethoxy)-cyclohexane, which is comprised of recurring units of the formula:

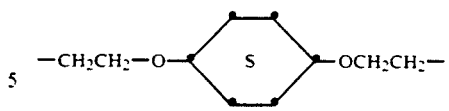

This polyester, referred to hereinafter as Polymer A, has been employed for many years in lithographic printing plates which have been extensively used on a commercial basis. These printing plates have typically employed an anodized aluminum substrate which has been formed by electrolytic anodization with an electrolyte comprised of phosphoric acid.

Polyesters in addition to Polymer A which are especially useful in the preparation of lithographic printing plates are those which incorporate ionic moieties derived from monomers such as dimethyl-3,3'-[(sodioimino)disulfonyl]dibenzoate and dimethyl-5-sodiosulfoisophthalate. Polyesters of this type are well known and are described, for example, in U.S. Pat. No. 3,929,489 issued Dec. 30, 1975. A preferred polyester of this type, referred to hereinafter as Polymer B, is poly[1,4-cyclohexylene-bis(oxyethylene)-p-phenylenediacrylate]-co-3,3'-[(sodioimino)disulfonyl]dibenzoate.

Another preferred polyester of this type, referred to hereinafter as Polymer C, is poly[1,4-cyclohexylene-bis-(oxyethylene)-p-phenylenediacrylate]-co-3,3'-[(sodioimino)disulfonyl]dibenzoate-co-3-hydroxyisophthalate.

Manufacturers of negative-working lithographic printing plates of the type described above typically incorporate a print-out composition in a radiation-sensitive layer of the plate which will produce an optical density difference upon exposure to activating radiation. This enables the customer to see the exposed image on the printing plate before it is processed.

A preferred technique for achieving such print-out is through the use of a print-out composition comprising a leuco form of a dye and a photooxidant. A particularly preferred class of photooxidants are photooxidants which have a photoscissionable nitrogen-oxygen bond, because they exhibit important advantages over other photooxidants, including the ability to provide improved print-out density. Examples of photooxidants having a photoscissionable nitrogen-oxygen bond are the sulfonyloxy-N photooxidants described in Altland et al, U.S. Pat. No. 4,425,424, issued Jan. 10, 1984. As explained by Altland et al, the leuco form of the dye has one or more removable hydrogen atoms, the removal of which forms a compound colored differently from the leuco form and the photooxidant, which is alternatively referred to as a photoactivator, is capable of converting the leuco dye to the differently colored form when exposed to the activating radiation. The photooxidants of the Altland et al patent are sulfonyloxy-N compounds of the formula:

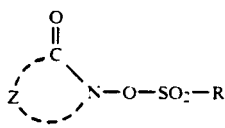

wherein R is a carbocyclic or heterocyclic ring containing from 5 to 10 ring atoms, and Z represents the nonmetallic atoms necessary to complete one or more rings containing from 5 to 17 ring atoms.

Further examples of photooxidants having a photoscissionable nitrogen-oxygen bond include the N,N,O-triacylhydroxylamines of U.S. Pat. No. 3,359,109; the O-acylthiohydroxamates and N-alkoxypyridinethiones of U.S. Pat. No. 4,954,415; the N-alkoxypyridinium salts of U.S. Pat. No. Re. 28,240; the oxycarbonyloxy-substituted pyridinium salts of U.S. Pat. No. 4,886,735; the oxime sulfonate esters of European Patent No. 361,907; and the oxime carboxylate esters of European Patent No. 332,158.

While print-out compositions containing photooxidants which have a photoscissionable nitrogen-oxygen bond provide useful results and are of great commercial importance, there is an urgent need in the art to improve the photo-efficiency of such print-out compositions. The print-out composition must generate sufficient dye density upon exposure to be readily observed without causing serious reduction in the speed of the plate. Thus, the print-out composition is typically employed in as small an amount as feasible in order not to dissipate an excessive amount of the exposure energy needed for the photoimaging components of the printing plate. This tends to result in too faint an image to be readily observable. Improvement in the photo-efficiency of the print-out composition is highly desirable, as it enables the production of a more distinct, and therefore more readily discernible print-out image, while avoiding any further loss in speed. Alternatively, improvements in photo-efficiency make possible further reductions in the concentration of print-out constituents so as to improve photospeed, while not detracting from the ability to discern a print-out image. Improvement in the photo-efficiency is very difficult to accomplish, since it must be achieved without deleteriously affecting the properties of the print-out composition or the radiation-sensitive polymer composition in which it is incorporated.

It is toward the objective of providing an improved radiation-sensitive composition comprising a photocrosslinkable polymer and a print-out composition with enhanced photo-efficiency that the present invention is directed.

SUMMARY OF THE INVENTION

In accordance with this invention, a heteroaromatic amine N-oxide is incorporated in a radiation-sensitive composition comprising (1) a photocross-linkable polymer containing the photosensitive group

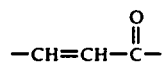

as an integral part of the polymer backbone; (2) a leuco form of a dye having one or more removable hydrogen atoms, the removal of which forms a compound colored differently from the leuco form; and (3) a photooxidant which has a photoscissionable nitrogen-oxygen bond, the photooxidant serving to convert the leuco dye to the differently colored form when the composition is exposed to activating radiation.

The incorporation of a heteroaromatic amine N-oxide in the radiation-sensitive composition dramatically increases the level of print-out. Thus, a readily discernible image can be achieved even though the print-out composition is employed in very small amounts. The most effective heteroaromatic amine N-oxides also provide the very important advantage of improved shelf-life in that there is little or no drop in print-out density resulting from storage of the printing plate. The heteroaromatic amine N-oxides are especially advantageous in that they are able to provide the enhanced photo-efficiency without deleteriously affecting the properties of the print-out composition or the radiation-sensitive polymer composition.

DESCRIPTION OF THE PREFERRED EMBODIMENTS

The print-out compositions utilized in the radiation-sensitive photocrosslinkable compositions of this invention are disclosed and claimed in copending, commonly assigned U.S. patent application Ser. No. 676,129, filed Mar. 27, 1991, "PRINT-OUT COMPOSITION USEFUL IN LITHOGRAPHIC PRINTING PLATES", by J. E. Mitchell et al.

Lithographic printing plates utilizing the radiation-sensitive photocrosslinkable compositions of this invention are disclosed and claimed in copending, commonly assigned U.S. Pat. application Ser. No. 676,130, filed Mar. 27, 1991, "LITHOGRAPHIC PRINTING PLATES", by J. E. Mitchell et al.

The present invention provides a major improvement in print-out compositions containing a leuco dye and a photooxidant which has a photoscissionable nitrogen-oxygen bond. The improvement is achieved by incorporation in the print-out composition of an effective amount of a heteroaromatic amine N-oxide, which functions to enhance the photoefficiency of the print-out composition.

Organic N-oxides of widely varying structure have been heretofore proposed for use in enhancing the speed of photosensitive compositions. In this regard, prior art of interest includes U.S. Pat. No. 3,481,739, which describes photosensitive compositions containing a color-forming compound, an activator and an organic N-oxide; U.S. Pat. No. 3,510,309 which describes similar photosensitive compositions which additionally contain a phenolic compounds that acts as an infrared stabilizer; U.S. Pat. No. 3,827,887 which describes photosensitive compositions containing a color-forming compound, an activator and an aromatic amine N-oxide, which both enhances speed and reduces susceptibility to moisture; and U.S. Pat. No. 4,066,459 which describes photosensitive compositions comprising compounds which contain an imine function and an hydroxyl group and which optionally contain an organic N-oxide.

Organic N-oxides have been heretofore proposed for use as photooxidants in photosensitive compositions. For example, pyridine N-oxides and quinoline N-oxides, or quaternary salts thereof, are utilized as photooxidants in U.S. Pat. No. 3,582,342.

Organic N-oxides have been heretofore proposed for use in photosensitive compositions for such purposes as preservatives, sensitizing agents, stabilizing agents and color development accelerators. Thus, for example, U.S. Pat. No. 4,251,619 refers to photosensitive compositions containing 4-phenylpyridine N-oxide, benzoquinoline N-oxide and 4-picoline N-oxide, and U.S. Pat. No. 4,640,886 refers to photosensitive compositions containing 4-picoline N-oxide.

Use of heteroaromatic amine N-oxides as agents to improve photo-efficiency in print-out compositions containing a leuco dye and a photooxidant which has a photoscissionable nitrogen-oxygen bond has not been disclosed in the prior art, and this combination is uniquely effective in providing enhanced print-out characteristics. These enhanced characteristics are especially beneficial in radiation-sensitive compositions comprising a photocrosslinkable polymer, and find particular advantage in negative-working lithographic printing plates where the print-out composition provides enhanced print-out without adversely affecting any of the many other important properties of such printing plates.

The radiation-sensitive compositions utilized in the lithographic printing plates described herein comprise photocrosslinkable polymers, such as polyesters, containing the photosensitive group

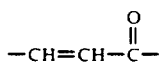

as an integral part of the polymer backbone. For example, preferred photocrosslinkable polymers are polyesters prepared from one or more compounds represented by the following formulae:

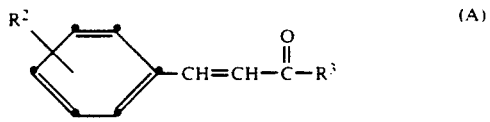

where $R^2$ is one or more alkyl of 1 to 6 carbon atoms, aryl of 6 to 12 carbon atoms, aralkyl of 7 to 20 carbon atoms, alkoxy of 1 to 6 carbon atoms, nitro, amino, acrylic, carboxyl, hydrogen or halo and is chosen to provide at least one condensation site; and $R^3$ is hydroxy, alkoxy of 1 to 6 carbon atoms, halo or oxy if the compound is an acid anhydride. A preferred compound is p-phenylene diacrylic acid or a functional equivalent thereof. These and other useful compounds are described in U.S. Pat. No. 3,030,208 (issued Apr. 17, 1962 to Schellenberg et al); U.S. Pat. No. 3,702,765 (issued Nov. 14, 1972 to Laakso); and U.S. Pat. No. 3,622,320 (issued Nov. 23, 1971 to Allen), the disclosures of which are incorporated herein by reference.

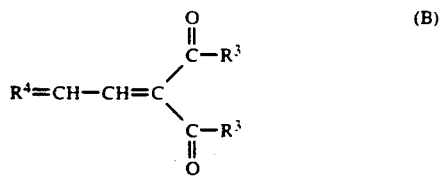

$R^3$ is as defined above, and $R^4$ is alkylidene of 1 to 4 carbon atoms, aralkylidene of 7 to 16 carbon atoms, or a 5- to 6-membered heterocyclic ring. Particularly useful compounds of formula (B) are cinnamylidenemalonic acid, 2-butenylidenemalonic acid, 3-pentenylidenemalonic acid, o-nitrocinnamylidenemalonic acid, naphthylallylidenemalonic acid, 2-furfurylideneethylidenemalonic acid and functional equivalents thereof. These and other useful compounds are described in U.S. Pat. No. 3,674,745 (issued Jul. 4, 1972 to Philipot et al), the disclosure of which is incorporated herein by reference.

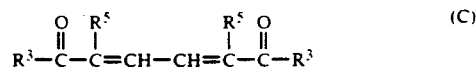

$R^3$ is as defined above; and $R^5$ is hydrogen or methyl. Particularly useful compounds of formula (C) are trans, trans-muconic acid, cis-transmuconic acid, cis, cis-muconic acid, $\alpha,\alpha'$-cis, trans-dimethylmuconic acid, $\alpha,\alpha'$-cis, cis-dimethylmuconic acid and functional equivalents thereof. These and other useful compounds are described in U.S. Pat. No. 3,615,434 (issued Oct. 26, 1971 to McConkey), the disclosure of which is incorporated herein by reference.

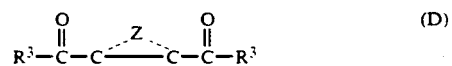

$R^3$ is as defined above; and Z represents the atoms necessary to form an unsaturated bridged or unbridged carbocyclic nucleus of 6 or 7 carbon atoms. Such nucleus can be substituted or unsubstituted. Particularly useful compounds of formula (D) are 4-cyclohexene-1,2-dicarboxylic acid, 5-norbornene-2,3-dicarboxylic acid, hexachloro-5[2:2:1]-bicycloheptene2,3-dicarboxylic acid and functional equivalents thereof. These and other useful compounds are described in Canadian Patent No. 824,096 (issued Sep. 30, 1969 to Mench et al), the disclosure of which is incorporated herein by reference.

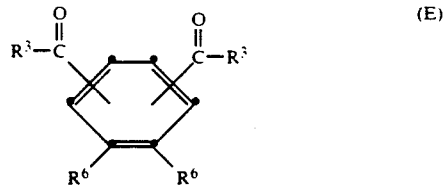

$R^3$ is as defined above; and $R^6$ is hydrogen, alkyl 1 to 12 carbon atoms, cycloalkyl of 5 to 12 carbon atoms or aryl of 6 to 12 carbon atoms. $R^6$ can be substituted where possible, with such substituents as do not interfere with the condensation reaction, such as halo, nitro, aryl, alkoxy, aryloxy, etc. The carbonyl groups are attached to the cyclohexadiene nucleus meta or para to each other, and preferably para. Particularly useful compounds of formula (E) are 1,3-cyclo-hexadiene-1,4-dicarboxylic acid, 1,3-cyclo-hexadiene-1,3-dicarboxylic acid, 1,5-cyclo-hexadiene-1,4-dicarboxylic acid and functional equivalents thereof. These and other useful compounds are described in Belgian Patent No. 754,892 (issued Oct. 15, 1970), the disclosure of which is incorporated herein by reference.

Preferred photocrosslinkable polyesters for use in this invention are p-phenylene diacrylate polyesters.

In addition to the photocrosslinkable polymer described above, the radiation-sensitive composition of this invention includes a print-out composition. The essential components of the print-out composition are (a) a leuco form of a dye having one or more removable hydrogen atoms, the removal of which forms a compound colored differently from the leuco form; (b) a photooxidant which has a photoscissionable nitrogen-oxygen bond and is capable of converting the leuco dye to the differently colored form when the composition is exposed to activating radiation; and (c) a heteroaromatic amine N-oxide which functions to improve the photo-efficiency of the print-out composition.

Any leuco dye that converts to a differently colored form upon the removal of one or more hydrogen atoms is useful in the present invention. Dyes that do not absorb significantly at the wavelengths used to activate the photopolymer are preferred. Most preferred are those leuco dyes in which the removable hydrogen(s) are not sterically hindered. Thus, useful leuco dyes are available from the classes set forth in U.S. Pat. Nos. 3,359,109 and 4,139,390, the disclosures of which are incorporated herein by reference. Included are aminotriarylmethanes, for example, 4,4',4"-methylidene-tris(N,N-dipropylaniline) and 4,4',4"-methylidene-tris(N,N-dimethylaniline); aminoxanthenes such as 3,6-bis(dimethylamino)-9-(p-dimethylaminophenyl)xanthene and 3,6-bis(diethylamino)-9-(p-dimethylaminophenyl)xanthene; aminothioxanthenes; aminophenoxazines; aminophenothiazines; aminodihydrophenazines, such as 3,6-bis(dimethylamino)-9-(p-dimethylaminophenyl)-phenazine and 3,7-bis(dimethylamino)-5,10-dihydro-5-phenylphenazine; aminodiphenylmethanes such as 1,1-bis(p-dimethylaminophenyl)methane; leuco indamines; aminohydrocinnamic acids such as 4-(p-chloroanilino)-α,β-dicyanohydrocinnamic acid, methyl ester and 4-anilino-α,β-dicyanohydrocinnamic acid, methyl ester; hydrazines such as 1-(2-naphthyl)-2-phenylhydrazine and 1-(p-dimethylaminophenyl)-2-(2-pyridyl)hydrazine; leuco indigoid dyes; amino-2,3-dihydroanthraquinones; and phenethylanilines such as N-(2-cyanoethyl)-p-phenethylaniline and N,N-diethyl-p-phenylethylaniline.

The photooxidants useful in this invention are those which have a photoscissionable nitrogen-oxygen bond. Thus, they are compounds which include within their structure the group:

The term "photoscissionable", as used herein, means capable of being split by the activating radiation, either directly such as by a photolysis mechanism or indirectly such as by electron transfer initiated by the activating radiation.

Sulfonyloxy-N photooxidants are compounds including in their structure the group:

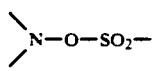

Especially effective compounds of this type are described in detail in Altland et al, U.S. Pat. No. 4,425,424, issued Jan. 10, 1984.

Useful sulfonyloxy-N photooxidants for the purpose of this invention include compounds of the formula:

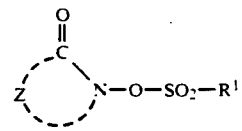

wherein:

R¹ is a carbocyclic or heterocyclic ring containing from 5 to 10 ring atoms, and Z represents the non-metallic atoms necessary to complete one or more rings containing from 5 to 17 ring atoms.

As used herein, "carbocyclic ring" and "heterocyclic ring" for R¹ of the photooxidant include both unsubstituted and substituted rings, such as aryl and substituted aryl such as phenyl, p-chlorophenyl, naphthyl, and the like. Other useful substituents on the carbocyclic or heterocyclic ring include halo-substituents such as bromo, and alkoxy such as methoxy. Useful heterocyclic rings include 2- or 3-thiophene; 2- or 3-furan; 2-, 3- or 4-pyridine; imidazole; triazole; and pyrazole.

Preferably Z represents the atoms necessary to provide a ring containing from 4 to 16 carbon atoms, producing, for example, a succinimide, glutarimide, phthalimide, napthalimide, pyridone or quinolone. Preferably, Z represents from 3 to 15 carbon atoms to form a cyclic moiety containing from one to four rings, optionally substituted with an oxy group adjacent to the nitrogen atom to form an additional ketone. Most preferably, Z represents such atoms which complete one to two rings.

Preferred sulfonyloxy-N photooxidants are those of the formula:

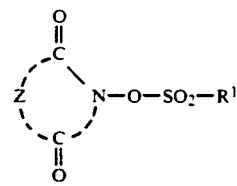

wherein R¹ and Z are as defined above.

Representative specific examples of sulfonyloxy-N photooxidants useful in this invention include N-(4-chlorobenzenesulfonyloxy)-1,8-naph-thalimide; N-(4-chlorobenzenesulfonyloxy)phthalimide; N-benzenesulfonyloxyphthalimide; N-benzenesulfonyloxy-1,8-naphthalimide; N-benzenesulfonyloxy-2(1H)-pyridone; and N-benzenesulfonyloxy-2(1H)-quinolone.

Phthalimides and naphthalimides represent preferred classes of sulfonyloxy-N photooxidants for use in this invention. Particularly preferred for use as the photooxidant is the compound N-(4-chlorobenzenesulfonyloxy)-1,8-naphthalimide which has the formula:

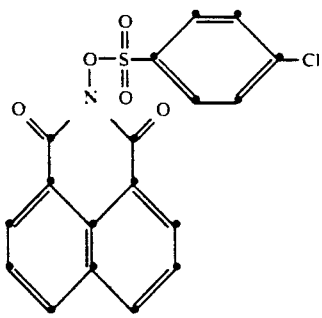

The N,N,O-triacylhydroxylamines are also very effective photooxidants for use in this invention. These are compounds of the formula:

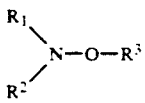

where each of $R^1$, $R^2$ and $R^3$ represents an acyl group. Examples of an acyl group include acetyl, propionyl, butyryl, n-octanoyl, n-decanoyl, stearoyl, benzoyl and naphthoyl.

As disclosed in Harder et al. U.S. Pat. No. 3,359,109 issued Dec. 19, 1967, representative N,N,O-triacylhydroxylamines which are particularly effective as photooxidants include:

N,N,O-triacetylhydroxylamine,
N,N,O-tripropionylhydroxylamine,
N,N,O-tributyrylhydroxylamine,
N,N,O-tristearoylhydroxylamine,
N,N,O-tribenzoylhydroxylamine,
N,N,O-tris(m-chlorobenzoyl)hydroxylamine,
N,N,O-tris(p-methylbenzoyl)hydroxylamine,
N,N,O-tris(o-propionylbenzoyl)hydroxylamine,
N,N-diacetyl-O-butyrylhydroxylamine,
N,N-diacetyl-O-benzoylhydroxylamine,
N,N-diacetyl-O-naphthoylhydroxylamine,
N,N-dibutyryl-O-acetylhydroxylamine,
N,N-dibenzoyl-O-acetylhydroxylamine,
N,N-dibenzoyl-O-(p-methylbenzoyl)hydroxylamine,
N,O-diacetyl-N-butyrylhydroxylamine,
N,O-diacetyl-N-benzoylhydroxylamine, and
N,O-dipropionyl-N-caproylhydroxylamine.

As also disclosed in the Harder et al patent, the N,N-acyl groups of the N,N,O-triacylhydroxylamine may, together with the nitrogen atom, form an imide ring to thereby produce an N-acyloxymide. Representative examples of such N-acyloxyimides include:

N-acetoxy-2,3-dimethylsuccinimide,
N-benzoyloxysuccinimide,
N-acetoxyglutarimide,
N-acetoxy-2-dodecylglutarimide,
N-butyryloxy-2,3-dimethylmaleimide,
N-(p-chlorobenzoyloxy)maleimide,
N-acetoxyphthalimide,
N-butyryloxyphthalimide,
N-benzoyloxyphthalimide,
N-(p-methylbenzoyloxy)phthalimide,
N-propionyloxy-2,3-naphthalimide,
N-(4-chlorobenzoyloxy)-1,8-naphthalimide
N-(4-cyanobenzoyloxy)phthalimide.

Another class of photooxidants which are very effective for use in this invention are the photooxidants described in U.S. Re. Pat. No. Re. 28,240, the disclosure of which is incorporated herein by reference. These are photooxidants which contain a heterocyclic nitrogen atom that is substituted by either an alkoxy group or an acyloxy group. As described in U.S. Pat. No. Re. 28,240, typical photooxidants of this class are represented by one of the formulas:

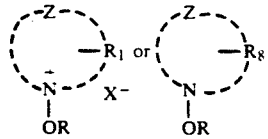

wherein
$R_1$ can be any of the following:
a. a methine linkage terminated by a heterocyclic nucleus of the type contained in cyanine dyes, e.g., those set forth in Mees and James, "The Theory of the Photographic Process," Macmillan, 3rd ed., pp. 198-232; the methine linkage can be substituted or unsubstituted, e.g., —CH=, —C(CH$_3$)=, —C(C$_6$H$_5$)=, —CH=CH—, —CH=CH—CH=, etc.;
b. an alkyl radical preferably containing one to eight carbon atoms including a substituted alkyl radical;
c. an aryl radical including a substituted aryl radical such as a phenyl radical, a naphthyl radical, a tolyl radical, etc.;
d. a hydrogen atom;
e. an acyl radical having the formula

wherein $R_9$ is hydrogen or an alkyl group preferably having one to eight carbon atoms;
f. an anilinovinyl radical such as a radical having the formula

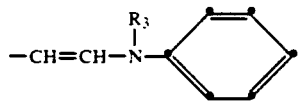

wherein $R_3$ is hydrogen, acyl or alkyl; or
g. a styryl radical including substituted styryl radicals, e.g.,

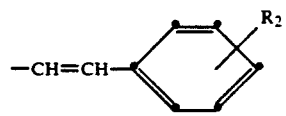

wherein $R_2$ is hydrogen, alkyl, aryl, amino, including dialkylamino such as dimethylamino;
$R_8$ can be either of the following:
a. a methine linkage terminated by a heterocyclic nucleus of the type contained in merocyanine dyes, e.g., those set forth in Mees and James (cited above); the methine linkage can be substituted or unsubstituted; or b. an allylidene radical including a substituted allylidene radical such as a cyanoallylidene radical, an alkylcarboxyallylidene radical or an alkylsulfonylallylidene radical;

R can be either:
a. an alkyl radical preferably having one to eight carbon atoms such as methyl, ethyl, propyl, butyl, etc., including a substituted alkyl radical such as sulfoalkyl, e.g., —(CH$_2$)$_3$SO$_3$—, an aralkyl, e.g., benzyl or pyridinatooxyalkyl salt, e.g., —(CH$_2$)$_3$—O—Y wherein Y is substituted or unsubstituted pyridinium salt; etc.,
b. an acyl radical, e.g.,

wherein R$_4$ is an alkyl radical preferably having one to eight carbon atoms or aryl radical, e.g., methyl, ethyl, propyl, butyl, phenyl, naphthyl, etc.

Z represents the atoms necessary to complete a five- to six-membered heterocyclic nucleus including a substituted heterocyclic nucleus, which nucleus can contain at least one additional heteroatom such as oxygen, sulfur, selenium or nitrogen, e.g., a pyridine nucleus, a quinoline nucleus, etc.; and X- represents an acid anion, e.g., chloride, bromide, iodide, perchlorate, sulfamate, thiocyanate, p-toluenesulfonate, methyl sulfate, tetrafluoroborate, etc.

Examples of photooxidants of the class described in Reissue U.S. Pat. No. Re. 28,240 which are especially preferred for use in this invention include:

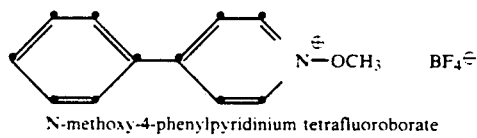

N-methoxy-4-phenylpyridinium tetrafluoroborate

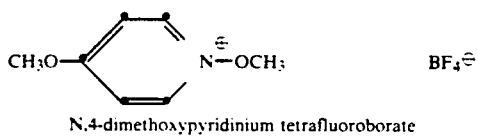

N,4-dimethoxypyridinium tetrafluoroborate

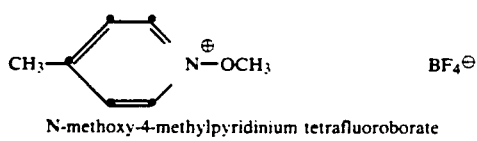

N-methoxy-4-methylpyridinium tetrafluoroborate

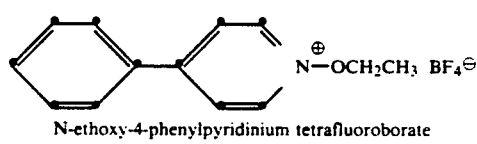

N-ethoxy-4-phenylpyridinium tetrafluoroborate

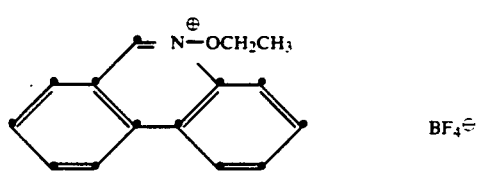

N-ethoxyphenanthridinium tetrafluoroborate

Many other types of photooxidants having a photoscissionable nitrogen-oxygen bond are also known to the art. Examples include:

(1) O-acylthiohydroxamates such as N-(3,3-diphenylpropionyloxy)-pyridine-2-thione, which has the formula:

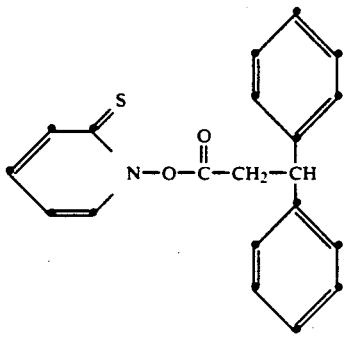

(2) oxycarbonyloxy-substituted pyridinium salts such as 1-(isobutoxycarbonyloxy)-2-picolinium chloride, which has the formula:

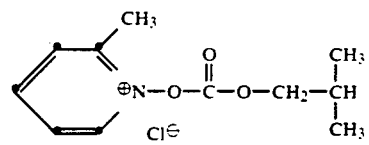

(3) oxime sulfonate esters such as o-(p-toluenesulfonyl)-α-hydroxyimino-benzylcyanide, which has the formula:

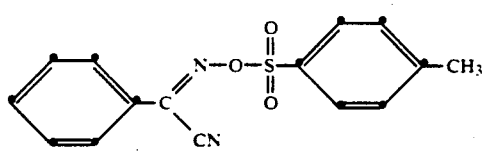

and o-(p-toluenesulfonyloxy)-9-fluorenone oxime, which has the formula:

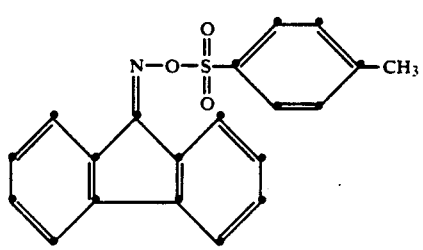

and (4) oxime carboxylate esters such as o-anisoylbenzophenone oxime, which has the formula:

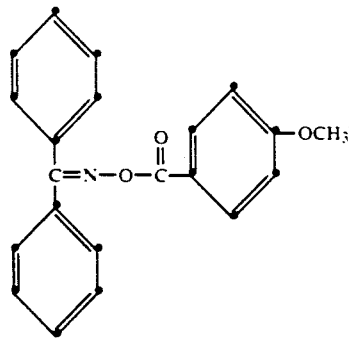

In accordance with this invention, a heteroaromatic amine N-oxide is used to provide improved photo-efficiency. By the term "heteroaromatic amine N-oxide" is meant a compound of the formula:

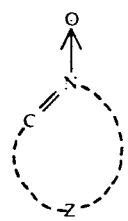

where Z represents the atoms necessary to complete one or more rings which may be substituted or unsubstituted.

In a preferred embodiment of the invention, the heteroaromatic amine N-oxide is a pyridine N-oxide. By the term "pyridine N-oxide" is meant a compound of the formula:

where Z' represents the atoms necessary to complete a pyridine ring which may be substituted or unsubstituted.

In a particularly preferred embodiment of the invention, the heteroaromatic amine N-oxide is a pyridine N-oxide of the formula:

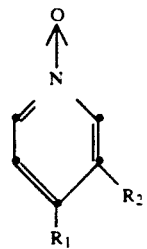

wherein one of $R_1$ and $R_2$ is hydrogen and the other is a

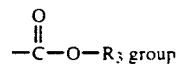

where $R_3$ is a substituted or unsubstituted alkyl group. $R_3$ is preferably alkyl of 1 to 20 carbon atoms and where the alkyl group is substituted, a preferred substituent is a dialkylamino group.

In the most preferred embodiments of the invention, the heteroaromatic amine N-oxide is an alkyl nicotinate N-oxide of the formula:

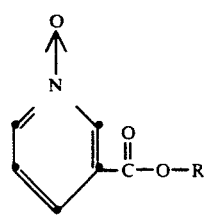

wherein R is an alkyl group of 2 to 20 carbon atoms, and more preferably 4 to 12 carbon atoms; or an N,N-dialkylnicotinamide N-oxide of the formula:

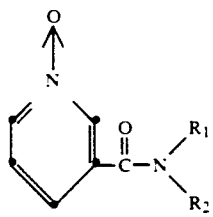

where each of $R_1$ and $R_2$ is an alkyl group of 1 to 20 carbon atoms, and more preferably of 2 to 6 carbon atoms.

In addition to the pyridine N-oxides, other examples of useful heteroaromatic amine N-oxides for the purpose of this invention include quinoline N-oxides, isoquinoline N-oxides and acridine N-oxides.

Specific examples of the many heteroaromatic amine N-oxides which are useful for the purpose of this invention include the following:

1.

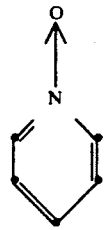

pyridine N-oxide

-continued
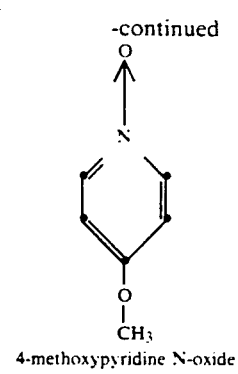
4-methoxypyridine N-oxide
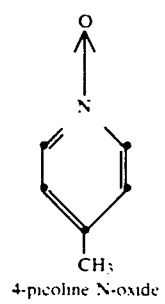
4-picoline N-oxide
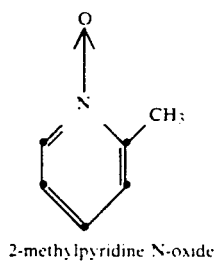
2-methylpyridine N-oxide
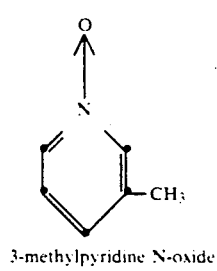
3-methylpyridine N-oxide
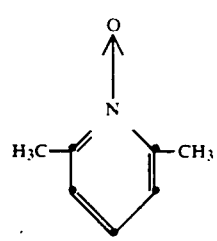
2,6-dimethylpyridine N-oxide
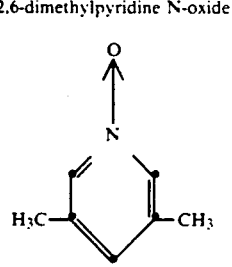
3,5-dimethylpyridine N-oxide
-continued
II.
III.
IV.
V.
VI.
VII.
VIII.
4-phenylpyridine N-oxide
IX.
2,2'-dithiobispyridine N-oxide
X.
4-decyloxypyridine N-oxide
XI.
ethyl nicotinate N-oxide
XII.
butyl nicotinate N-oxide -continued
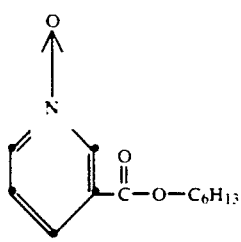
hexyl nicotinate N-oxide
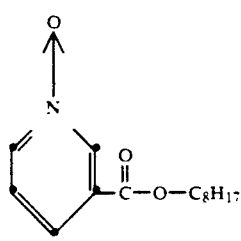
octyl nicotinate N-oxide
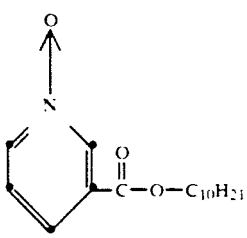
decyl nicotinate N-oxide
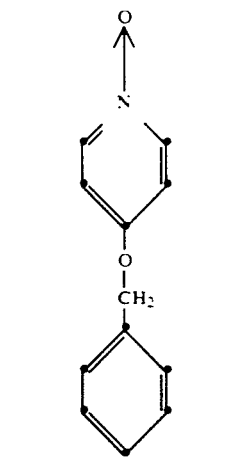
4-benzyloxypyridine N-oxide
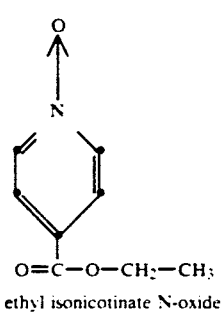
ethyl isonicotinate N-oxide
-continued
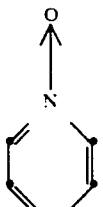
4-cyanopyridine N-oxide
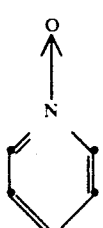
4-nitropyridine N-oxide
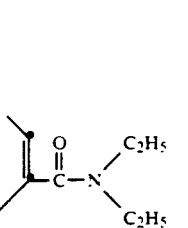
N,N-diethylnicotinamide N-oxide
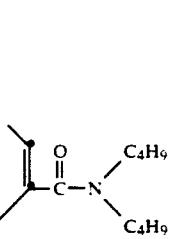
N,N-dibutylnicotinamide N-oxide
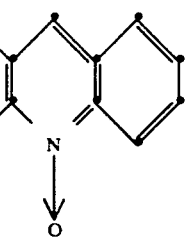
acridine N-oxide
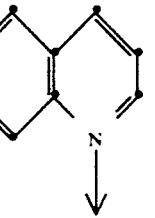
quinoline N-oxide

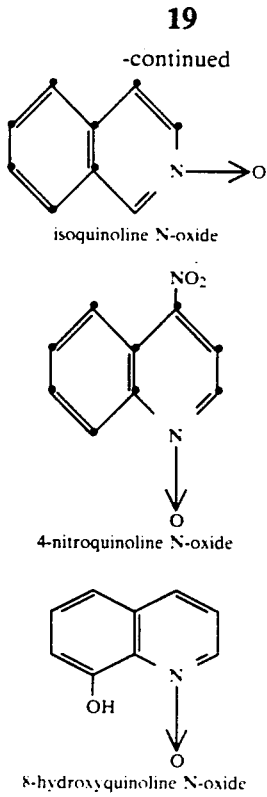

isoquinoline N-oxide 4-nitroquinoline N-oxide 8-hydroxyquinoline N-oxide

The heteroaromatic amine N-oxides employed in this invention are either known compounds or can be readily synthesized from well known starting materials.

For purposes of illustration of suitable synthetic methods, the synthesis of compounds X, XIV and XV is described below:

Synthesis of Compound X (4-decyloxypyridine N-oxide)

4-Nitropyridine N-oxide (5.0 g., 30 mmol), decyl alcohol (19 g. 120 mmol), tetrabutylammonium bromide (0.5 g, 1.6 mmol) and potassium carbonate (8.2 g, 60 mmol) were stirred and heated in acetonitrile (30 mL) for 16 hours. The resulting mixture was then filtered to remove insoluble material and the filtrate was evaporated under reduced pressure. The residue was dissolved in ether, washed with water, dried over anhydrous sodium sulfate, filtered and evaporated. The crude product was twice recrystallized from ligroine to give 4.31 g of 4-decyloxypyridine N-oxide, mp 57°–65° C.

Synthesis of Compound XIV (octyl nicotinate N-oxide)

Hydrogen chloride was bubbled through cold octanol (25 g, 190 mmol) until a weight gain of 4.2 g had registered. Nicotinic acid N-oxide (5.29 g, 38 mmol) was then added and the resulting mixture was stirred and heated at 95°–100° C. for 3 hours and 40 minutes. The excess octanol was then removed by distillation at reduced pressure, and the residue of the distillation was taken up in dichloromethane. The dichloromethane solution was washed with aqueous sodium bicarbonate and then with water, dried over anhydrous magnesium sulfate, filtered and evaporated under reduced pressure. The residue was recrystallized from ligroine to give 7.73 g (31 mmol) of octyl nicotinate N-oxide, mp 69.5°–71° C.

Synthesis of Compound XV (decyl nicotinate N-oxide)

Nicotinic acid N-oxide (5.00 g, 36 mmol), decyl alcohol (5.86 g, 37 mmol) and methanesulfonic acid (3.70 g, 38.5 mmol) were stirred and heated to reflux in toluene (50 mL), in a flask equipped with a condenser and a Dean-Stark trap for 19 hours. The reaction mixture was then cooled, diluted with ether and washed successively with water, aqueous sodium bicarbonate and brine. The toluene/ether solution was then dried over anhydrous magnesium sulfate, filtered and evaporated under reduced pressure. The residue was recrystallized from ligroine (100 mL) to give 7.50 g (27 mmol) of decyl nicotinate N-oxide, mp 80.5° C.

The mechanism whereby the heteroaromatic amine N-oxides function in this invention is not clearly understood. It is believed that an important factor relating to storage stability is the degree to which the heteroaromatic amine N-oxide tends to volatilize and thereby to escape from the printing plate composition. Both the type of substituents and their bulk are believed to be significant factors affecting the performance of the heteroaromatic amine N-oxides. Both electron donating and electron withdrawing substituents have been found to provide dramatically enhanced print-out density.

Advantages provided by use of heteroaromatic amine N-oxides in accordance with this invention include a very substantial increase in the level of print-out and excellent shelf-life characteristics. A further unexpected benefit of the heteroaromatic amine N-oxides is the ability to reduce or eliminate "residual print-out". This problem can occur when processed printing plates are brought out to white light in press room areas and are partially covered with other plates before going to press. Plates which do not include the heteroaromatic amine N-oxide become darker in the uncovered areas, leading to concern about the ability of the plate to print uniformly, whereas this darkening does not occur with the printing plates of this invention.

The lithographic printing plates described herein comprise a support having coated thereon a layer containing the radiation-sensitive composition described above. Such plates can be prepared by forming coatings with the coating composition and removing the solvent by drying at ambient or elevated temperatures. Any one of a variety of conventional coating techniques can be employed, such as extrusion coating, doctor-blade coating, spray coating, dip coating, whirl coating, spin coating, roller coating, etc.

Coating compositions containing the photocrosslinkable polymers described herein can be prepared by dispersing or dissolving the polymer in any suitable solvent or combination of solvents used in the art to prepare polymer dopes. The solvents are chosen to be substantially unreactive toward the polymer within the time period contemplated for maintaining the solvent and polymer in association and are chosen to be compatible with the substrate employed for coating. While the best choice of solvent will vary with the exact application under consideration, exemplary preferred solvents include alcohols, such as butanol and benzyl alcohol; ketones, such as acetone, 2-butanone and cyclohexanone; ethers such as tetrahydrofuran and dioxane; 2-methoxyethyl acetate; N,N'-dimethylformamide; chlorinated hydrocarbons such as chloroform, trichloroethane, 1,2-dichloroethane, 1,1-dichloroethane, 1,1,2-trichloroethane, dichloromethane, tetrachloroethane, chlorobenzene; and mixtures thereof.

Suitable supports can be chosen from among a variety of materials which do not directly chemically react with the coating composition. Such supports include fiber based materials such as paper, polyethylene-coated paper, polypropylene-coated paper, parchment, cloth, etc.; sheets and foils of such materilas as aluminum, copper, magnesium, zinc, etc.; glass and glass coated with such metals as chromium alloys, steel, silver, gold, platinum, etc.; synthetic resin and polymeric materials such as poly(alkyl acrylates), e.g., poly(methyl methacrylate), polyester film base, e.g., poly(ethylene terephthalate), poly(vinyl acetals), polyamides, e.g., nylon and cellulose ester film base, e.g., cellulose nitrate, cellulose acetate, cellulose acetate propionate, cellulose acetate butyrate and the like.

Preferred support materials include zinc, anodized aluminum, grained aluminum, and aluminum which has been grained and anodized. Particularly preferred support materials are described in Miller et al, U.S. Pat. No. 4,647,346, issued Mar. 3, 1987, and Huddleston et al, U.S. Pat. No. 4,865,951, issued Sep. 12, 1989.

The support can be preliminarily coated—i.e., before receipt of the radiation-sensitive coating—with known subbing layers such as copolymers of vinylidene chloride and acrylic monomers—e.g., acrylonitrile, methyl acrylate, etc. and unsaturated dicarboxylic acids such as itaconic acid, etc.; carboxymethyl cellulose, gelatin; polyacrylamide; and similar polymer materials. A preferred subbing composition comprises benzoic acid and is described in Miller et al, U.S. Pat. No. 4,640,886, issued Feb. 3, 1987.

The optimum coating thickness of the radiation-sensitive layer will depend upon such factors as the particular application to which the printing plate will be put, and the nature of other components which may be present in the coating. Typical coating thicknesses can be from about 0.05 to about 10.0 microns or greater, with thicknesses of from 0.1 to 2.5 microns being preferred.

The printing plates described herein can be exposed by conventional methods, for example, through a transparency or a stencil, to an imagewise pattern of actinic radiation, preferably rich in ultraviolet light, which crosslinks and insolubilizes the radiation-sensitive polymer in the exposed areas. Suitable light sources include carbon arc lamps, mercury vapor lamps, fluorescent lamps, tungsten filament lamps, "photoflood" lamps, lasers and the like. The exposure can be by contact printing techniques, by lens projection, by reflex, by bireflex, from an image-bearing original or by any other known technique.

The exposed printing plate can be developed by flushing, soaking, swabbing or otherwise treating the crosslinked radiation-sensitive composition with a solution (hereinafter referred to as a developer) which selectively solubilizes (i.e., removes) the unexposed areas of the radiation-sensitive layer. The developer is preferably an aqueous solution having a pH as near to neutral as is feasible.

In a preferred form, the developer includes a combination of water and an alcohol that is miscible with water, or able to be rendered miscible by the use of cosolvents or surfactants, as a solvent system. The proportions of water and alcohol can be varied widely but are typically within the range of from 40 to 99 percent by volume water and from 1 to 60 percent by volume alcohol. Most preferably, the water content is maintained within the range of from 60 to 90 percent by volume. Any alcohol or combination of alcohols that does not chemically adversely attack the crosslinked radiation-sensitive layer during development and that is miscible with water in the proportions chosen for use can be employed. Exemplary of useful alcohols are glycerol, benzyl alcohol, 2-phenoxy-ethanol, 1,2-propanediol, sec-butyl alcohol and ethers derived from alkylene glycols—i.e., dihydroxy poly(alkylene oxides)—e.g., dihydroxy poly(ethylene oxide), dihydroxy poly(propylene oxide), etc.

It is recognized that the developer can, optionally, contain additional addenda. For example, the developer can contain dyes and/or pigments. It can be advantageous to incorporate into the developer anti-scumming and/or anti-blinding agents as is well recognized in the art.

A preferred developing composition for use with the novel lithographic printing plates described herein is an aqueous composition including:

(a) a nontoxic developing vehicle, such as butyrolactone, phenoxy propanol, phenoxy ethanol, benzyl alcohol or methyl pyrrolidone, which is a non-solvent for any of the components of the lithographic plate;

(b) a first surfactant comprising a sodium, lithium or potassium salt of xylene sulfonic acid;

(c) a second surfactant comprising a sodium, lithium or potassium salt of toluene, ethyl benzene, cumene or mesitylene sulfonic acid;

(d) a third surfactant comprising a sodium, lithium or potassium salt of an alkyl benzene sulfonic acid, the alkyl group containing at least ten carbon atoms, or an alkyl naphthalene sulfonic acid, the alkyl group containing from one to four carbon atoms;

(e) a cold water soluble film-forming agent such as polyvinyl pyrrolidone, polystyrene/maleic anhydride copolymers, polyvinyl alcohol, polyvinyl methyl ethers and polystyrene/vinyl acetate copolymers;

(f) an alkanolamine desensitizing agent such as diethanolamine; and (g) an acid, such as citric, ascorbic, tartaric, glutaric, acetic, phosphoric, sulfuric or hydrochloric acid, to control the pH of the developing composition.

These developing compositions are described in copending commonly assigned U.S. patent application Ser. No. 379,823, filed Jul. 14, 1989, "Aqueous Developer Composition For Developing Negative-Working Lithographic Printing Plates", by J. E. Walls, the disclosure of which is incorporated herein by reference. A developing composition of this type is commercially available from Eastman Kodak Company, Rochester, N.Y., as KODAK AQUEOUS PLATE DEVELOPER MX-1469-1.

After development, the printing plate can be treated in any known manner consistent with its intended use. For example, lithographic printing plates are typically subjected to desensitizing etches.

In addition to the photocrosslinkable polymer, the leuco dye, the photooxidant and the heteroaromatic amine N-oxide, a number of other addenda can be present in the coating composition and ultimately form a part of the completed printing plate. For example, radiation sensitivity of the radiation-sensitive polymeric composition can be enhanced by incorporating therein one or more spectral sensitizers. Suitable spectral sensitizers include anthrones, nitro sensitizers, triphenylmethanes, quinones, cyanine dyes, naphthones, pyrylium and thiapyrylium salts, furanones, anthraquinones, 3-ketocoumarins, thiazoles, thiazolines, naphthothiazolines, quinalizones, and others described in U.S. Pat.

No. 4,139,390 and references noted therein. Preferred sensitizers include the 3-ketocoumarins described in U.S. Pat. No. 4,147,552 and the thiazoline sensitizers of U.S. Pat. No. 4,062,686. Such sensitizers can be present in the compositions in effective sensitizing amounts easily determined by one of ordinary skill in the art.

While applicants do not wish to be bound by any theoretical explanation of the manner in which their invention functions, it is believed that the spectral sensitizer may also interact with the photooxidant under the influence of the activating radiation and contribute to scission of the nitrogen-oxygen bond of the photooxidant by an energy transfer mechanism.

The coating composition can contain pigments preferably having a maximum average particle size less than about 3 micrometers. These pigments can provide a visible coloration to an image before or after development of the element. Useful pigments are well known in the art and include titanium dioxide, zinc oxide, copper phthalocyanines, halogenated copper phthalocyanines, quinacridine, and colorants such as those sold commercially under such trade names as Monastral Blue and Monastral Red B. The pigments are generally present in the compositions in an amount within the range of from 0 to about 50 percent (by weight) based on the total dry composition weight. Preferred amounts are within the range of from about 5 to about 20 percent (by weight).

It is recognized that the radiation-sensitive compositions described herein can become crosslinked prior to intended exposure if the compositions or printing plates of this invention are stored at elevated temperatures, in areas permitting exposure to some quantity of actinic radiation and/or for extended periods of time. To insure against crosslinking the composition inadvertently before intended exposure to actinic radiation, stabilizers can be incorporated therein. Useful stabilizers include picoline N-oxide; phenols, such as 2,6-di-tert-butyl-p-cresol, 2,6-di-tert-butylanisole and p-methoxyphenol; hydroquinones such as hydroquinone, phloroglucinol and 2,5-di-tert-butylhydroquinone; triphenylmetallics, such as triphenylarsine; triphenylstilbene; and tertiary amines, such as N-methyldiphenylamine.

Still other addenda useful in the printing plates described herein include antioxidants, surfactants, antiscumming agents, and others known in the art.

Binders or extenders can optionally be incorporated into the radiation-sensitive composition. Such binders or extenders can be present in an amount within the range of from 0 to about 50 percent (by weight) based on total dry composition weight. Suitable binders include styrene-butadiene copolymers; silicone resins; styrene-alkyd resins; silicone-alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals), such as poly(vinyl butyral); polyacrylic and -methacrylic esters, such as poly(methyl methacrylate), poly(n-butyl methacrylate) and poly(isobutyl methacrylate); polystyrene; nitrated polystyrene; polymethylstyrene; isobutylene polymers; polyesters, such as poly(ethylene-co-alkaryloxyalkylene terephthalate); phenolformaldehyde resins; ketone resins; polyamides; polycarbonates; polythiocarbonates, poly(ethylene 4,4'-isopropylidenediphenylene terephthalate); copolymers of vinyl acetate such as poly(vinyl-m-bromobenzoate-co-vinyl acetate); ethyl cellulose, poly(vinyl alcohol), cellulose acetate, cellulose nitrate, chlorinated rubber and gelatin. Methods of making binders or extenders of this type are well known in the prior art. A typical resin of the type contemplated for use is Piccolastic A50 TM, commercially available from Hercules, Inc., Wilmington, Del. Other types of binders which can be used include such materials as paraffin and mineral waxes.

The print-out compositions described herein can be utilized wherever it is desired to provide a visible color change upon exposure to activating radiation. They can be used not only in printing plates, but in diverse decorative, protective and imaging applications. They are useful in any of the many types of radiation-sensitive compositions wherein a visual print-out of the exposure is desired; for example they can be used in photoresists employed in the manufacture of printed circuit boards. The print-out compositions are especially useful in combination with photocrosslinkable polymers to provide a negative-working lithographic printing plate composition, particularly those wherein the photocrosslinkable polymer contains the photosensitive group

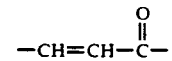

as an integral part of the polymer backbone. Other types of lithographic printing plates, including printing plates containing diazonium compounds—such as the condensation product of p-diazo diphenyl amine and paraformaldehyde—can also benefit from use of the novel print-out compositions described herein.

It should be noted that heteroaromatic amine N-oxides can perform more than one function in radiation-sensitive compositions of the type described herein. Thus, for example, 4-picoline N-oxide has been disclosed in the prior art for use as a photooxidant, as a sensitizer and as a stabilizer. In this invention, it is used to improve the photo-efficiency of the print-out composition.

The print-out system described herein utilizes a leuco dye, a photooxidant which has a photoscissionable nitrogen-oxygen bond and a heteroaromatic amine N-oxide. These three agents can be used in any effective amount, depending on the particular application involved. Typically, the leuco dye is employed in an amount of from about 0.0001 to about 0.1 parts per part by weight of photocrosslinkable polymer, the photooxidant is employed in an amount of from 0.0005 to about 0.2 parts per part by weight of photocrosslinkable polymer, and the heteroaromatic amine N-oxide is employed in an amount of from about 0.0002 to about 0.2 parts per part by weight of photocrosslinkable polymer.

The invention is further illustrated by the following examples of its practice. In these examples, the photocrosslinkable polymer is Polymer A identified hereinabove, but similar results are also achieved with lithographic printing plates comprising other photocrosslinkable polymers containing the photosensitive group

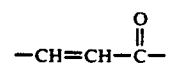

such as, for example, Polymer B or Polymer C described hereinabove. Mixtures of two or more photocrosslinkable polymers such as mixtures of Polymers A, B and C can also be employed.

EXAMPLES 1-5

A coating composition useful in preparing lithographic printing plates was prepared in accordance with the following formulation:

| Component | Amount (grams) |
|---|---|
| (1) Polymer A (15% by weight solution in 1,2-dichloroethane) | 90.10 |
| (2) PICCOLASTIC A-50 resin* | 1.94 |
| (3) MONASTRAL Red pigment (7% by weight dispersion in 1,2-dichloroethane) | 32.22 |
| (4) 2-[Bis(2-furoyl)methylene]-1-methyl-naphtho[1,2-d] thiazoline | 0.52 |
| (5) 2,6-Di-t-butyl-p-cresol | 0.38 |
| (6) N-(4-Chlorobenzenesulfonyloxy)-1,8-naphthalimide | 0.88 |
| (7) Dihydroanhydropiperidinohexose reductone | 0.02 |
| (8) Leuco propyl violet | 0.16 |
| (9) MODAFLOW coating aid** | 0.50 |
| (10) 1,2-Dichloroethane | 373.28 |

*PICCOLASTIC A-50 is the trademark for a polystyrene resin supplied by Hercules, Inc.
**MODAFLOW coating aid is a copolymer of ethyl acrylate and 2-ethylhexyl acrylate manufactured by Monsanto Corporation In the above-formulation, (1) and (2) serve as film-forming polymers, (3) serves as a colorant, (4) serves as a spectral sensitizer, (5) serves as a stabilizer, (6) serves as a photooxidant, (7) serves as an antioxidant, (8) serves as a print-out dye, (9) serves as a coating aid and (10) serves as a solvent.

The above-described formulation contains no heteroaromatic amine N-oxide additive, and was utilized as a control coating, for comparison with coatings within the scope of the invention containing heteroaromatic amine N-oxides, as indicated in Table 1 below. In each instance, the heteroaromatic amine N-oxide was added in an amount of 3.22 millimoles.

Printing plates were prepared by coating the radiation-sensitive composition, over a phosphoric acid-anodized aluminum substrate provided with a thin carboxymethyl cellulose subcoat, to give a dry coating weight of the radiation-sensitive layer of approximately 1.3 g/m$^2$. Samples of each coating were given 17 units of exposure on an OLEC vacuum frame (manufactured by OLEC CORPORATION of Irvine, Calif.) and then the print-out density was determined by subtracting the optical density of the unexposed regions from that of the exposed regions of each plate. The same print-out density determinations were made for samples of each plate which had been baked in a forced air oven for 2 minutes at 110° C. The results obtained are reported in Table 1.

TABLE 1

| Test No. | Heteroaromatic Amine N-oxide | Print-Out Density As Coated | Baked |
|---|---|---|---|
| Control | None | 0.04 | 0.04 |
| Example 1 | Compound II | 0.14 | 0.11 |
| Example 2 | Compound III | 0.14 | 0.06 |
| Example 3 | Compound IX | 0.09 | 0.06 |
| Example 4 | Compound X | 0.14 | 0.16 |
| Example 5 | Compound XV | 0.10 | 0.13 |

As indicated by the data in Table 1, all of the heteroaromatic amine N-oxides increased the print-out density substantially beyond the value of 0.04 that was obtained with the control. The bake treatment serves as a prediction of the long term stability of the print-out material. In this regard, particularly good results were obtained in Examples 1, 4 and 5. In the case of 4-picoline N-oxide (Compound III), a drop in print-out density is noticeable between freshly coated plates and plates which are only one day old. On the other hand, in the case of decyl nicotinate N-oxide (Compound XV), no change in print-out density has been observed, even after storage under ambient conditions for two months. The relative sensitometric speeds of the control plate and the Example 5 plate were determined to be 127 and 134, respectively; indicating that the addition of the decyl nicotinate N-oxide resulted in no loss of speed.

EXAMPLES 6-10

Printing plates were prepared from the same formulation described with regard to Examples 1-5 and, in each case, a heteroaromatic amine N-oxide as indicated in Table 2 was added in an amount of 3.22 millimoles. Samples of each coating were given 18 units of exposure on the OLEC vacuum frame, and then the print-out density was determined. The same print-out density determinations were made for samples of each plate which had been baked in a forced air oven for 2 minutes at 105° C. The results obtained are reported in Table 2.

TABLE 2

| Test No. | Heteroaromatic Amine N-oxide | Print-Out Density As Coated | Baked |
|---|---|---|---|
| Example 6 | Compound XI | 0.12 | 0.08 |
| Example 7 | Compound XII | 0.12 | 0.11 |
| Example 8 | Compound XIII | 0.11 | 0.11 |
| Example 9 | Compound XIV | 0.11 | 0.12 |
| Example 10 | Compound XV | 0.11 | 0.12 |

As indicated by the data in Table 2, all of the heteroaromatic amine N-oxides increased the print-out density substantially beyond the value of 0.04 that is obtained when no heteroaromatic amine N-oxide is utilized.

The samples of Examples 6 and 10 were aged for five and a half months under ambient conditions. Measurements were made of the unexposed density, the exposed density and the print-out density for both fresh and aged samples, and the results obtained are reported in Table 3 below.

TABLE 3

| Sample | Unexposed Density Fresh | Aged | Exposed Density Fresh | Aged | Print-Out Density Fresh | Aged |
|---|---|---|---|---|---|---|
| Example 6 | 0.66 | 0.64 | 0.76 | 0.69 | 0.10 | 0.05 |
| Example 10 | 0.63 | 0.64 | 0.72 | 0.73 | 0.09 | 0.09 |

The above results indicate that there is less loss in print-out density with aging for decyl nicotinate N-oxide (Compound XV) than for ethyl nicotinate N-oxide (Compound XI). This result is believed to be, at least in part, due to the fact that more of the ethyl nicotinate N-oxide is lost due to volatilization from the printing plate.

The samples of Examples 4, 6, 7, 8, 9 and 10 were incubated for two weeks at 49° C. Measurements were made of the unexposed density, the exposed density and the print-out density for both fresh and incubated samples, and the results obtained are reported in Table 4 below.

TABLE 4

| Sample | Unexposed Density Fresh | Unexposed Density Incubated | Exposed Density Fresh | Exposed Density Incubated | Print-Out Density Fresh | Print-Out Density Incubated |
|---|---|---|---|---|---|---|
| Control | 0.64 | 0.67 | 0.68 | 0.70 | 0.04 | 0.03 |
| Example 4 | 0.59 | 0.64 | 0.74 | 0.71 | 0.15 | 0.07 |
| Example 6 | 0.60 | 0.60 | 0.72 | 0.68 | 0.12 | 0.08 |
| Example 7 | 0.60 | 0.61 | 0.72 | 0.70 | 0.12 | 0.09 |
| Example 8 | 0.61 | 0.61 | 0.71 | 0.69 | 0.10 | 0.08 |
| Example 9 | 0.60 | 0.61 | 0.71 | 0.69 | 0.11 | 0.08 |
| Example 10 | 0.61 | 0.61 | 0.72 | 0.69 | 0.11 | 0.08 |

As shown by the data in Table 4, for the control coating the print-out density remained more or less constant with incubation, despite the fact that the background or unexposed density increased, presumably due to thermal oxidation of the leuco propyl violet. For the coatings containing the alkyl nicotinate N-oxides of Examples 6 to 10, the print-out density dropped a little on incubation, but the background density remained essentially unchanged, so that the print-out contrast remained high. With the 4-decyloxypyridine N-oxide of Example 4, the coating not only exhibited a small loss in exposed density with incubation, but also a significant increase in background density on incubation (from 0.59 to 0.64) so that the net change in print-out density was quite large (from 0.15 to 0.07). Thus, even though 4-decyloxypyridine N-oxide initially provides print-out densities superior to those of the alkyl nicotinate N-oxides, the latter are preferred as print-out enhancing materials, since the print-out contrast changes very little with time. It has also been observed that coating compositions containing the alkyl nicotinate N-oxides show much less darkening on aging than do similar compositions without heteroaromatic amine N-oxide additives or similar compositions containing 4-alkoxypyridine N-oxides.

The samples of Examples 1 and 2 were allowed to age under ambient conditions for three months. Measurements were made of the unexposed density, the exposed density and the print-out density for both fresh and aged samples, and the results are reported in Table 5 below.

TABLE 5

| Sample | Unexposed Density Fresh | Unexposed Density Aged | Exposed Density Fresh | Exposed Density Aged | Print-Out Density Fresh | Print-Out Density Aged |
|---|---|---|---|---|---|---|
| Example 1 | 0.64 | 0.64 | 0.78 | 0.71 | 0.14 | 0.07 |
| Exmaple 2 | 0.65 | 0.67 | 0.79 | 0.76 | 0.14 | 0.09 |

The results reported in Table 5 indicate that the plate containing 4-picoline N-oxide (Example 2) lost 36% of its print-out density, due in part to an increase in background density. The plate containing 4-methoxypyridine N-oxide (Example 1) lost 50% of its print-out density, even though there was no increase in background density on aging at room temperature.

EXAMPLES 11-17

Printing plates were prepared from the same formulation described with regard to Examples 1-5 and, in each case, a heteroaromatic amine N-oxide as indicated in Table 6 was added in an amount of 3.22 millimoles. Unexposed density, exposed density and print-out density were measured before and after incubating the coatings for one week at 80% relative humidity and 27° C.

TABLE 6

| Test No. | Heteroaromatic Amine N-oxide | Unexposed Density Fresh | Unexposed Density Incubated | Exposed Density Fresh | Exposed Density Incubated | Print-Out Density Fresh | Print-Out Density Incubated |
|---|---|---|---|---|---|---|---|
| Example 11 | Compound XVI | 0.65 | 0.66 | 0.77 | 0.70 | 0.12 | 0.04 |
| Example 12 | Compound VIII | 0.65 | 0.66 | 0.77 | 0.72 | 0.12 | 0.06 |
| Example 13 | Compound XI | 0.65 | 0.65 | 0.75 | 0.74 | 0.10 | 0.09 |
| Example 14 | Compound XVII | 0.66 | 0.65 | 0.76 | 0.72 | 0.10 | 0.07 |
| Example 15 | Compound XVIII | 0.65 | 0.64 | 0.75 | 0.68 | 0.10 | 0.04 |
| Example 16 | Compound XIX | 0.66 | 0.66 | 0.76 | 0.71 | 0.10 | 0.05 |
| Example 17 | Compound XX | 0.56 | 0.56 | 0.65 | 0.66 | 0.09 | 0.10 |

As indicated by the data in Table 6, all of the heteroaromatic amine N-oxides increased the print-out density substantially beyond the value that is obtained when no heteroaromatic amine N-oxide is utilized. Each of Examples 11 through 16 suffered a loss of effectiveness on incubation, but the ethyl nicotinate N-oxide of Example 13 clearly suffered the least loss. The best results were achieved with the N,N-diethylnicotinamide N-oxide of Example 17, which exhibited no loss in print-out density with incubation.

EXAMPLE 18

A control coating composition was prepared that was identical to that described above with reference to Examples 1-5. In the same manner as described hereinabove, printing plates were prepared from the control composition and from a test composition containing 3.22 millimoles of octyl nicotinate N-oxide. Samples of each coating were given 18 units of exposure on an OLEC vacuum frame and machine processed with KODAK AQUEOUS PLATE DEVELOPER MX-1469-1. The exposed and processed plates were then partially masked with an opaque film and re-exposed to 72 units of light. As shown in Table 7 below, no density difference could be measured between the masked and re-exposed areas after the second exposure for the test coating containing octyl nicotinate N-oxide, whereas a measureable difference was present for the control coating.

TABLE 7

|  | Density Under Masked Area | Density Under Re-Exposed Area |
|---|---|---|
| Control Coating | 0.57 | 0.59 |
| Test Coating | 0.58 | 0.58 |

As indicated by the data in Table 7, the octyl nicotinate N-oxide eliminated the problem of residual print-out.

EXAMPLE 19

A control coating composition was prepared that was identical to that described above with reference to Examples 1-5 except that the N-(4-chlorobenzenesulfonyloxy)-1,8-naphthalimide was replaced with an equimolar amount of N-(4-cyanobenzoyloxy)phthalimide. In the same manner as described hereinabove, printing plates were prepared from the control composition and from a test composition containing 3.22 millimoles of octyl nicotinate N-oxide. Samples of each coating were given 18 units of exposure on an OLEC vacuum frame, and density readings were taken in the exposed and unexposed areas. The results obtained are reported in Table 8.

TABLE 8

|  | Unexposed Density | Exposed Density | Print Out Density |
|---|---|---|---|
| Control Coating | 0.55 | 0.59 | 0.04 |
| Test Coating | 0.55 | 0.64 | 0.09 |

As indicated by the data in Table 8, the heteroaromatic amine N-oxide provided a substantial increase in print-out density in a composition utilizing an N,N,O-triacylhydroxylamine photooxidant.

EXAMPLE 20

A control coating composition was prepared that was identical to that described above with reference to Examples 1-5 except that Polymer A was of somewhat higher molecular weight and the N-(4-chlorobenzenesulfonyloxy)-1,8-naphthalimide was replaced with an equimolar amount of N-methoxy-4-phenylpyridinium tetrafluoroborate. In the same manner as described hereinabove, printing plates were prepared from the control composition and from a test composition containing 3.22 millimoles of octyl nicotinate N-oxide. Samples of each coating were given 6.6 units of exposure on an OLEC vacuum frame, and density readings were taken in the exposed and unexposed areas. The results obtained are reported in Table 9.

TABLE 9

|  | Unexposed Density | Exposed Density | Print Out Density |
|---|---|---|---|
| Control Coating | 0.55 | 0.61 | 0.06 |
| Test Coating | 0.55 | 0.67 | 0.12 |

As indicated by the data in Table 9, the heteroaromatic amine N-oxide provided a substantial increase in print-out density in a composition utilizing an N-alkoxypyridinium salt photooxidant.

The print-out compositions described herein provide many important advantages which render them especially useful in lithographic printing plates. For example, they are compatible with the polymers and solvents typically employed in preparing the radiation-sensitive layer of a lithographic printing plate. They provide excellent print-out density so that the desired image is readily visible. They can be employed in very small amounts so as not to interfere with the activation of the photopolymer, yet still provide sufficient dye density to be readily observed. The enhancement in print-out produced by addition of a heteroaromatic amine N-oxide does not result in any decrease in photospeed beyond that caused by the presence of the photooxidant and leuco dye. The most effective species provide excellent shelf-life characteristics, since the printing plate can be stored for extended periods without serious loss of the print-out density, and effectively avoid the problem of residual print-out.

The invention has been described in detail with particular reference to preferred embodiments thereof, but it will be understood that variations and modifications can be effected within the spirit and scope of the invention.

We claim:

1. A radiation-sensitive composition useful in the production of negative-working lithographic printing plates, said composition comprising a photocrosslinkable polymer containing the photosensitive group

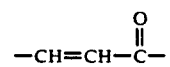

as an integral part of the polymer backbone and a print-out composition which produces an optical density difference upon exposure to activating radiation; said print-out composition comprising (a) a leuco form of a dye having one or more removable hydrogen atoms, the removal of which forms a compound colored differently from the leuco form, (b) a photooxidant which has a photoscissionable nitrogen-oxygen bond, said photooxidant functioning to convert said leuco dye to said differently colored form upon exposure to said activating radiation, and (c) a heteroaromatic amine N-oxide which functions to improve the photo-efficiency of said print-out composition.

2. A radiation-sensitive composition as claimed in claim 1, wherein said photocrosslinkable polymer is a p-phenylene diacrylate polyester.

3. A radiation-sensitive composition as claimed in claim 1 wherein said photocrosslinkable polymer is comprised of recurring units of the formula:

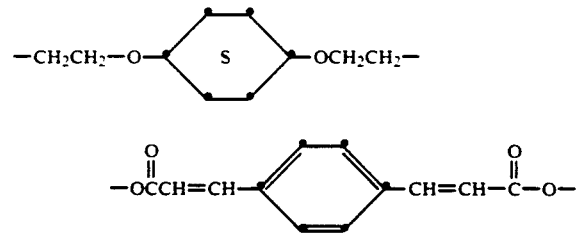

4. A radiation-sensitive composition as claimed in claim 1 wherein said leuco dye is an aminotriarylmethane dye.

5. A radiation-sensitive composition as claimed in claim 1 wherein said leuco dye is leuco propyl violet.

6. A radiation-sensitive composition as claimed in claim 1 wherein said photooxidant is a sulfonyloxy-N photooxidant.

7. A radiation-sensitive composition as claimed in claim 1 wherein said photooxidant is an N,N,O-triacylhydroxylamine.

8. A radiation-sensitive composition as claimed in claim 1 wherein said photooxidant is a N-acyloxyimide.

9. A radiation-sensitive composition as claimed in claim 1 wherein said photooxidant is represented by the formula:

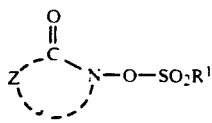

wherein:
R¹ is a carbocyclic or heterocyclic ring containing from 5 to 10 ring atoms, and
Z represents the non-metallic atoms necessary to complete one or more rings containing from 5 to 17 ring atoms.

10. A radiation-sensitive composition as claimed in claim 1 wherein said photooxidant is represented by the formula:

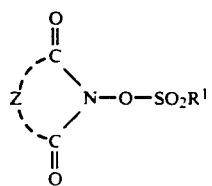

wherein:
R¹ is a carbocyclic or heterocyclic ring containing from 5 to 10 ring atoms, and
Z represents the non-metallic atoms necessary to complete one or more rings containing from 5 to 17 ring atoms.

11. A radiation-sensitive composition as claimed in claim 1 wherein said photooxidant is N-(4-chlorobenzenesulfonyloxy)1,8-naphthalimide.

12. A radiation-sensitive composition as claimed in claim 1 wherein said photooxidant is N-(4-cyanobenzoyloxy)phthalimide.

13. A radiation-sensitive composition as claimed in claim 1 wherein said photooxidant contains a heterocyclic nitrogen atom that is substituted by either an alkoxy group or an acyloxy group.

14. A radiation-sensitive composition as claimed in claim 1 wherein said photooxidant is an N-alkoxypyridinium salt.

15. A radiation-sensitive composition as claimed in claim 1 wherein said photooxidant is N-methoxy-4-phenylpyridinium tetrafluoroborate.

16. A radiation-sensitive composition as claimed in claim 1 wherein said heteroaromatic amine N-oxide is a pyridine N-oxide.

17. A radiation-sensitive composition as claimed in claim 1 wherein said heteroaromatic amine N-oxide is a pyridine N-oxide of the formula:

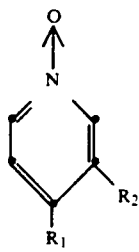

wherein one of R₁ and R₂ is hydrogen and the other is a

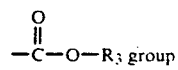

where R₃ is alkyl.

18. A radiation-sensitive composition as claimed in claim 1 wherein said heteroaromatic amine N-oxide is an alkyl nicotinate N-oxide of the formula:

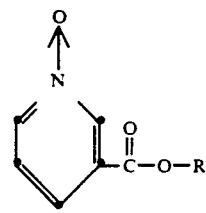

where R is alkyl.

19. A radiation-sensitive composition as claimed in claim 1 wherein said heteroaromatic amine N-oxide is an N,N-dialkylnicotinamide N-oxide of the formula:

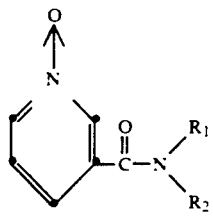

where each of R₁ and R₂ is alkyl.

20. A radiation-sensitive composition as claimed in claim 1 wherein said heteroaromatic amine N-oxide is 4-methoxypyridine N-oxide.

21. A radiation-sensitive composition as claimed in claim 1 wherein said heteroaromatic amine N-oxide is 2.2'-dithiobis-pyridine N-oxide.

22. A radiation-sensitive composition as claimed in claim 1 wherein said heteroaromatic amine N-oxide is decyl nicotinate N-oxide.

23. A radiation-sensitive composition as claimed in claim 1 wherein said heteroaromatic amine N-oxide is octyl nicotinate N-oxide.

24. A radiation-sensitive composition as claimed in claim 1 wherein said heteroaromatic amine N-oxide is N,N-diethylnicotinamde N-oxide.

25. A radiation-sensitive composition as claimed in claim 1 wherein said heteroaromatic amine N-oxide is 4-nitroquinoline N-oxide.

26. A radiation-sensitive composition comprising a photocrosslinkable polymer comprised of recurring units of the formula:

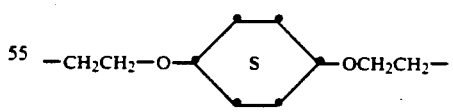

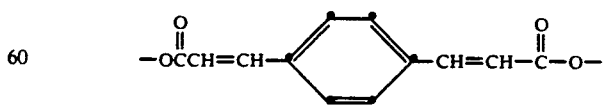

and a print-out composition which produces an optical density difference upon exposure to activating radiation; said print-out composition comprising (a) leuco propyl violet, (b) N-(4-chlorobenzene-sulfonyloxy)-1,8-naphthalimide and (c) octyl nicotinate N-oxide.

* * * * *